US010430749B2

(12) United States Patent
Le Couedic et al.

(10) Patent No.: US 10,430,749 B2
(45) Date of Patent: Oct. 1, 2019

(54) METHOD AND SYSTEM FOR MONITORING THE USE OF SENSITIVE PRODUCTS

(75) Inventors: Régis Le Couedic, Bordeaux (FR); Erick Cloix, Camblanes (FR)

(73) Assignee: GLOBAL HEALTHCARE EXCHANGE, LLC, Louisville, CO (US)

( * ) Notice: Subject to any disclaimer, the term of this patent is extended or adjusted under 35 U.S.C. 154(b) by 566 days.

(21) Appl. No.: 13/028,389

(22) Filed: Feb. 16, 2011

(65) Prior Publication Data

US 2011/0208535 A1    Aug. 25, 2011

(30) Foreign Application Priority Data

Feb. 17, 2010   (FR) ...................................... 10 00659

(51) Int. Cl.
*G06Q 10/08*   (2012.01)
*G06Q 50/22*   (2018.01)
*G16H 40/20*   (2018.01)

(52) U.S. Cl.
CPC ........... *G06Q 10/08* (2013.01); *G06Q 10/087* (2013.01); *G06Q 50/22* (2013.01); *G16H 40/20* (2018.01)

(58) Field of Classification Search
None
See application file for complete search history.

(56) References Cited

U.S. PATENT DOCUMENTS

| 5,725,578 A | 3/1998 | Knapp et al. |
| 5,969,970 A | 10/1999 | Rhoades |
| 7,473,097 B2 | 1/2009 | Raby et al. |

(Continued)

FOREIGN PATENT DOCUMENTS

| DE | 19614719 A1 | 10/1997 |
| FR | 2776790 A1 | 10/1999 |

(Continued)

OTHER PUBLICATIONS

U.S. Appl. No. 51/172,552 Specification, Whole Document filed Apr. 24, 2009.*

(Continued)

*Primary Examiner* — Neal Sereboff
(74) *Attorney, Agent, or Firm* — Snell & Wilmer L.L.P.

(57) ABSTRACT

Certain embodiments of the invention relate to a method for monitoring the use of sensitive products (16) in which the products and/or their packaging are marked and identified and then the products are marketed while storing successively their references in a CENTRAL FILE, associated with determined user customers and with suppliers, then in stock-management files (30, 30') and, gradually as they are used at a user customer, in customer files (34, 34', etc.).

If one or more anomalies are found making it possible to qualify a product of determined type as defective ($R_D$), data comprising the reference of the defective product can be automatically and simultaneously transmitted to all of the media of the various files, the reference of the defective product is automatically compared (35, 35', etc.) with the product references appearing in the files, and in the event of a positive comparison, a warning signal is immediately or substantially immediately triggered.

20 Claims, 3 Drawing Sheets

(56) References Cited

U.S. PATENT DOCUMENTS

| | | | |
|---|---|---|---|
| 2001/0037220 A1 | 11/2001 | Merry et al. | |
| 2001/0056359 A1* | 12/2001 | Abreu | G06K 7/10861 705/3 |
| 2004/0008123 A1 | 1/2004 | Carrender et al. | |
| 2004/0256469 A1 | 12/2004 | Faenza et al. | |
| 2005/0010448 A1 | 1/2005 | Mattera | |
| 2006/0089888 A1 | 4/2006 | Roger | |
| 2006/0138221 A1 | 6/2006 | Swan et al. | |
| 2006/0232408 A1 | 10/2006 | Nycz et al. | |
| 2006/0235488 A1* | 10/2006 | Nycz | A61B 90/90 607/60 |
| 2007/0299421 A1 | 12/2007 | Gibson | |
| 2010/0274591 A1* | 10/2010 | Wells | G06Q 10/06 705/3 |
| 2011/0093400 A1* | 4/2011 | Waite | G06Q 30/014 705/303 |
| 2011/0093401 A1* | 4/2011 | Waite | G06Q 30/014 705/303 |

FOREIGN PATENT DOCUMENTS

| | | |
|---|---|---|
| FR | 2865193 A | 7/2005 |
| FR | 2878053 A | 5/2006 |
| JP | 2002-132927 | 5/2002 |
| WO | 1996039099 A | 12/1996 |
| WO | 1999066444 A | 12/1999 |
| WO | 2001035872 A | 5/2001 |
| WO | 2004008387 | 1/2004 |
| WO | 2004008387 A | 1/2004 |
| WO | 2004008387 A1 | 1/2004 |
| WO | 2005098736 | 10/2005 |
| WO | 2006108026 | 10/2006 |
| WO | 2008043921 A2 | 4/2008 |

OTHER PUBLICATIONS

U.S. Appl. No. 51/172,552 Appendix to the Specification filed Apr. 24, 2009.*
Definition—"associated" as downloaded on Oct. 21, 2015.*
Definition—"resctricting" as downloaded on Oct. 21, 2015.*
International Search Report FR Application No. 10/00659 dated Sep. 15, 2010.
Pending related U.S. Appl. No. 12/444,735 Entitled: Method and System for Tracking Medical Products, filed Apr. 8, 2009, (Publication No. US 2010/0096454 A1, publication date—Apr. 22, 2010).
Article—Henning Baars Et al: "Combining RFID Technology and Business Intelligence for Supply Chain A Optimization Scenarios for Retail Logistics" Hawaii International Conference on System Sciences, Proceedings of the 41st Annual IEEE, Piscataway, NJ, USA, Jan. 1, 2008 (Jan. 1, 2008), p. 73.
International Search Report in PCT/FR2007/001675, 3 pages, dated Jul. 8, 2008.
Written Opinion dated Sep. 12, 2012 in Application No. PCT/FR2011/000095.
International Preliminary Report on Patentability dated Sep. 18, 2012 in Application No. PCT/FR2011/000095.
Notice of Allowance dated Jul. 22, 2011 in U.S. Appl. No. 12/444,735.
Office Action dated Sep. 14, 2010 in U.S. Appl. No. 12/444,735.
Office Action dated Jun. 8, 2011 in Australian Application No. 2007306266.
International Preliminary Report on Patentability dated May 5, 2009 in Application No. PCT/FR2007/001675.
Office Action dated Nov. 19, 2013 in Korean Application No. 2009-7009512.
Office Action dated Nov. 11, 2013 in Japanese Application No. 2009-531880.
Office Action dated Mar. 18, 2013 in Japanese Application No. 2009-531880.
Office Action dated Sep. 16, 2014 in Canadian Application No. 2,666,247.
Final Rejection dated May 19, 2014 in Korean Application No. 2009-7009512.
Office Action dated May 20, 2015 in Canadian Application No. 2,666,247.
Rejection dated Apr. 10, 2015 in Japanese Application No. 2009-531880.
Notice of Allowance dated Jan. 15, 2016 in Japanese Application No. 2014-4544.
Office Action dated Jan. 4, 2016 in European Application No. 11709992.9.
Notice of Allowance dated Mar. 1, 2016 in Canadian Application No. 2,666,247.
Examination Report dated Dec. 19, 2016 in Indian Application No. 2431/DELNP/2009.
Office Action dated Nov. 8, 2018 in France Application No. 1000659.

* cited by examiner

METHOD AND SYSTEM FOR MONITORING THE USE OF SENSITIVE PRODUCTS

Certain aspects of the present invention relate to a method and a system of monitoring the use of sensitive products corresponding to a determined type, allowing a perfect traceability of the latter, notably for the purposes of insurance and quality recall.

"A product corresponding to a determined type" means products having physical, chemical or biological characteristics that are identical or similar.

It finds a particularly important, although not exclusive, application in the field of medical products and notably of implantable medical devices such as internal prostheses (knees, hips, etc.). But, more generally, it is also applicable to all industrial fields involving products that are sensitive and for which quality recalls may be demanded.

One application is, for example, in the field of medicine monitoring. By making it possible, in particular, to gain virtually instantaneous access to the users of hazardous products that have been introduced onto the market, such an application will make it possible to stop them and/or recall them quickly.

Currently there is essentially one known method of recalls in the event of a quality problem, which is as follows:

Based on the analysis of events, defects in design or machining of a type of product, for example an implant, are put forward for which it is decided to recall one or more manufacturing batches.

The clinics and hospitals to which the batches concerned have been shipped are then informed by mail of the necessity to isolate and return the products belonging to the incriminated batches.

Such a method may have drawbacks.

Specifically, first of all and in most cases, the clinics and hospitals may have only human resources for trying to locate the products that are to blocked or returned. If the stocks are dispersed in several locations (supply rooms, operation units, operating rooms), the search is particularly awkward.

Very often, the first recall letter produces little effects. It is then necessary either to dispatch a representative of the manufacturer on site when possible, or to send new follow-up letters.

After a certain delay and several letters, and even in the event of an incomplete return, the recall is closed by the manufacturer with a result that is therefore not very satisfactory.

More precisely, several important failings may appear throughout this procedure.

They are notably due to the fact that, having no means of knowing the end customer (the patient) of the medical device, the manufacturer cannot himself carry out the quality recall to the end of the chain.

Moreover, he has no means of forcing the clinic or the hospital into a diligent management of the actions involved in this quality recall, nor does he have means of knowing the proportion of incriminated batches already implanted/still in stock.

In summary, the manufacturer has no means of really and sufficiently securing the quality recall, by notably preventing the care centres from using the incriminated products, on the one hand whether they have not correctly received the information, and on the other hand, whether they have not actually blocked the products.

One variation of the invention provides a method and a system for monitoring the use of sensitive products such as notably medical products, notably that allows a traceability and a quality monitoring of the products in a reliable and uninterrupted manner, from the manufacturer to the patient, while automating and considerably simplifying their logistics.

The contentious product may be immediately identified in its marketing chain and can be flagged and stopped without a delay that is harmful to the patients while thus ensuring a quality recall hitherto impossible to achieve, because of the lack of a satisfactory method for implementing it, while minimizing the costs thereof.

Certain variations of the invention therefore allow the professionals to satisfy a health requirement which has unsuccessfully been sought to place in service for many years.

Moreover, with some variations of the invention, the hospital, paramedical and/or medical staff have practically no more manual intervention to carry out, which increases safety by minimizing the risk of human error.

The immediate identification of patients concerned for a problem that has occurred or is potential on a type of implant or medicine also becomes possible, which is a considerable advantage, possibly saving human lives.

Also in some variations of the invention, the management for the medical bodies such as hospitals, pharmacies or medical practices, for the suppliers of medicines and/or of implants, and for doctors becomes extremely easy by virtue of permanent and immediate access, through all means of sorting or of analyses of data, to all and/or some of the databases concerning the products in question.

For this purpose, one variation of the invention proposes essentially a method for monitoring the use of sensitive products corresponding to a determined type, in which the products and/or their packaging are marked and identified with a first reference including a second reference corresponding to the determined type, which is stored in one or more first product-reference files, called supplier files, then the products are marketed while storing successively the first references of the products in a second file called a central file, associated with corresponding determined user customers and with the suppliers, in third respective stock-management files of the user customers and, gradually as they are used at a user customer, in fourth files each associated with the use for a patient of the user customer concerned, characterized in that, if one or more anomalies are found making it possible to qualify a product of a determined type as defective, automatically and simultaneously from the media of the first files, data is transmitted comprising the second reference of the defective product to all of the media of the second, the third and fourth files, or transmitted from the second file to the first, third and fourth files, the second defective product reference is automatically compared with the second product references appearing in the first or second and third and fourth files, and in the event of a positive comparison, a warning signal is immediately or substantially immediately triggered to and/or on the medium or media associated with the files to which the positive comparison relates.

With certain variations of the invention, it is therefore possible to carry out an automatic, immediate, real time or virtually real time dispatch of the quality recall notices to all of the establishments concerned, once such a recall is decided.

It is then possible to carry out an automatic, immediate and simultaneous quarantining of the identified products at whatever place in the logistics chain they may be. This function ensures that these products cannot continue to be dispatched even if they are not physically at the manufacturer, thus immediately stopping the "pollution" of the logistics chain.

In advantageous embodiments, use is also made of one and/or other of the following arrangements:

when the second reference corresponding to the product is inserted into the fourth file, and after positive comparison identifying it as defective, the continuation and/or the validation of the operation associated with the creation or with the modification of the fourth file is prevented in order to block the use for the patient.

The automatic, immediate and simultaneous installation of such a computer lock thus prevents the use of the incriminated products at the ultimate, pre-operative stage, and does so as a function of the patient himself.

In other words, this lock associated with an alarm being triggered when there is an attempt to use one of the recalled products prevents the product from being included in the patient file. It is therefore possible to thus prevent its use even without waiting for the effective time separating the dispatch of the recall letter and the physical blocking of the products by the recipients.

This is therefore an additional guarantee that the recall will be diligently taken into account by the sites concerned:

the warning signal comprises a visual message and/or an audible signal;
the product is a surgical implant;
the product is a medicine;
the products and/or their packaging are marked and identified with the first reference by optical recognition means;
the products and/or their packaging are marked and identified with the first reference by radioelectric or RFID recognition means;
the first references of the products of which the second references have been identified as corresponding to those of a defective product, and a file name or a file location in which the second references have been identified are automatically or semi-automatically transmitted to the central file and/or to the supplier file(s), and the product is taken off the market.

In some embodiments there is thus an automatic, immediate and simultaneous modification, at source, of all of the files containing products originating from the manufacturing batches to be recalled:

the internet may be used to interrogate, and communicate between, the first, second, third and fourth files;
the second references of the products appearing in the various files may be compared in order to ascertain the proportion of incriminated products that have been used and those that are still in stock or in transit;
the first product references may be automatically and remotely detected at the time of delivery which are stored in the third file,
the removal from the stock may be automatically detected,
the first product references may be inserted into the fourth file corresponding to the patient of the user customer for whom it will be used,
and in the event of no transmission of a warning signal following a negative comparison, a fifth file may be formed comprising partial references of the patient (maintaining medical confidentiality) and the first product references for tracing and this fifth file may be automatically or semi-automatically transmitted to a centralized database for subsequent monitoring;
the second references being associated with a sixth file of product references incompatible with the products corresponding to the second references, the content of the fifth file corresponding to the patient with that of the sixth file may be compared before use of the product corresponding to the second references and, in the event of positive comparison, the use of the product is blocked.

In this embodiment, the system of placing computer locks (in the form of alarms which are triggered when there is an attempt to include a medical device in the patient file, for example by reading an RFID chip) prevents the use of the product in combination with the incompatible product already used.

In the case of an application to the monitoring of implants, it is therefore possible to prevent the occurrence of the problems associated with:

the use, in combination, of incompatible materials,
the use, in combination, of inappropriate sizes of implants that may comprise the mechanical hold of the assembly,
the use, in combination, of incompatible implants, which is of particular value when launching new products or during periods of transition or of evolution of products.

Certain variations of the invention also propose a method as described above in which the means for marking and identifying the product also comprises a card secured to an RFID label contained in the packaging of the product, the card comprising a seventh file comprising in its entirety or in part the first reference of the product and specifying one or more of its characteristics (dimensions, etc.), its material, its condition of use, the pathologies incompatible with its use and/or the types of allergy that it may cause, the content of the seventh file is compared with the fourth file of identification with a patient, the date or dates and the types of intervention carried out on the patient, and all the data relating to the products used on the patient in order to identify the risks of incompatibility before use of the product corresponding to the first reference and, in the event of a positive comparison, the use of the product is blocked.

Some embodiments of the invention also propose a system using the method as described above.

It also proposes a system for monitoring sensitive products corresponding to a determined type, comprising means for marking and identifying the products and/or their packagings with a first reference including a second reference corresponding to the determined type, means for storing the first references in one or more first files (e.g., a computer and/or associated storage media), called supplier files, means for storing the first references of the products in a second file (e.g., a computer and/or associated storage media) called a central file associated with determined user customers and with the suppliers, means for storage after transport of the packaged products to the user customers (e.g., a computer and/or associated storage media) for the purpose of their subsequent use for patients, means for storage in the third respective stock-management files of the user customers (e.g., a computer and/or associated storage media) and, means for storage in fourth files each of the fourth files being associated with a patient of the determined customer (e.g., a computer and/or associated storage media), gradually as the products are used, characterized in that it also comprises
in the event of one or more anomalies being found making it possible to qualify a product of determined type as defective,
means of automatic and simultaneous transmission of data (e.g., a computer) comprising the second reference of the defective product to all of the means for storage of the second or first and third and fourth files,
means for comparing the reference of the determined type of the defective product with the second references of the products appearing in the second or first and third and fourth files (e.g., a computer),
and means of immediate or virtually immediate transmission of a warning signal (e.g., buzzer, light, displayed message) to the means of storage associated with the files concerned in the event of a positive comparison. The system may also comprise subsets of the above-described system.

"Virtually immediate" means within a reasonable period, for example less than one day.

Advantageously, it comprises means for blocking the continuation and/or the validation (e.g., a computer) of the operation associated with the creation or with the modification of the fourth file during the insertion of the second reference corresponding to the product in the fourth file, and after positive comparison identifying it as defective, in order to block the use for the patient.

In an advantageous embodiment, the means for transmitting a warning signal comprises means for sending a visual message and/or an audible signal.

In another advantageous embodiment, the system comprises means for marking (e.g., bar code, RFID tags, smart cards) and detecting the implants and/or their packagings by optical recognition and/or comprises means for marking and detecting the implants and/or their packagings by radioelectric or RFID recognition.

Advantageously, it may comprise means arranged to use the internet and for interrogating and communicating between files (e.g., a computer).

Also advantageously, it may comprise means of automatic or semi-automatic transmission to the central file, and/or to the supplier file(s) (e.g., a computer), of the first references of the products of which the second references have been identified as corresponding to those of a defective product and the coordinates of the file or files in which the second references have been identified, in order to take the product off the market.

"Semi-automatic" means in two or more stages, requiring at least an additional external action, such as a human approval for example.

Also advantageously, it may comprise means for comparing (e.g., a computer) the second references of the products appearing in the various files in order to ascertain the proportion of incriminated products that have been used and those that are still in stock or in transit.

In advantageous embodiments, use may also be made of one and/or other of the following arrangements:
the system comprises means of automatic and remote detection of the first references of the product at the time of delivery which are stocked in the third file,
means of automatic detection of the removal from the stock,
means for insertion, for example manual insertion, of the first references of the product into the fourth file (e.g., a computer) corresponding to the patient of the user customer for which it will be used,
and in the event of no transmission of a warning signal following a negative comparison, means for forming a fifth file (e.g., a computer) comprising partial references of the patient (maintaining medical confidentiality) and the first references of the product for tracing and automatic or semi-automatic transmission of this fifth file to a centralized database for subsequent monitoring.

This fifth file maintains medical confidentiality for example by encryption and/or allocation of a one-to-one number guaranteeing confidentiality.
the second references being associated with a sixth file of product references incompatible with the products corresponding to the second references, it comprises means for comparing (e.g., a computer) the contents of the fifth file corresponding to the patient with that of the sixth file before use of the product corresponding to the second references and, in the event of a positive comparison, means for signalling the incompatible nature of the product (e.g., a buzzer, display, or computer message);
the means for marking and identifying the product may comprise a card secured to an RFID label contained in the packaging of the product, the card comprising a seventh file comprising wholly or partly the first reference of the product, the system comprises means for comparing the content of the seventh file with the fourth identification file of a patient (e.g., a computer), the date or dates and the types of intervention carried out on the patient, and all the data relating to the products used on the patient, in order to identify the risks of incompatibility before use of the product corresponding to the first reference and, in the event of a positive comparison, the means for signalling the incompatibility of the product.

The one-to-one number and its correspondence with the name-related data of a patient may be known only to the authorized medical staff, which ensures confidentiality.

The invention will be better understood on reading the following description of embodiments given as non-limiting examples.

The description refers to the drawings which accompany it in which:

FIG. 1 shows schematically a diagram 1 illustrating principles of a method used according to certain variations of the invention.

Figure 1:
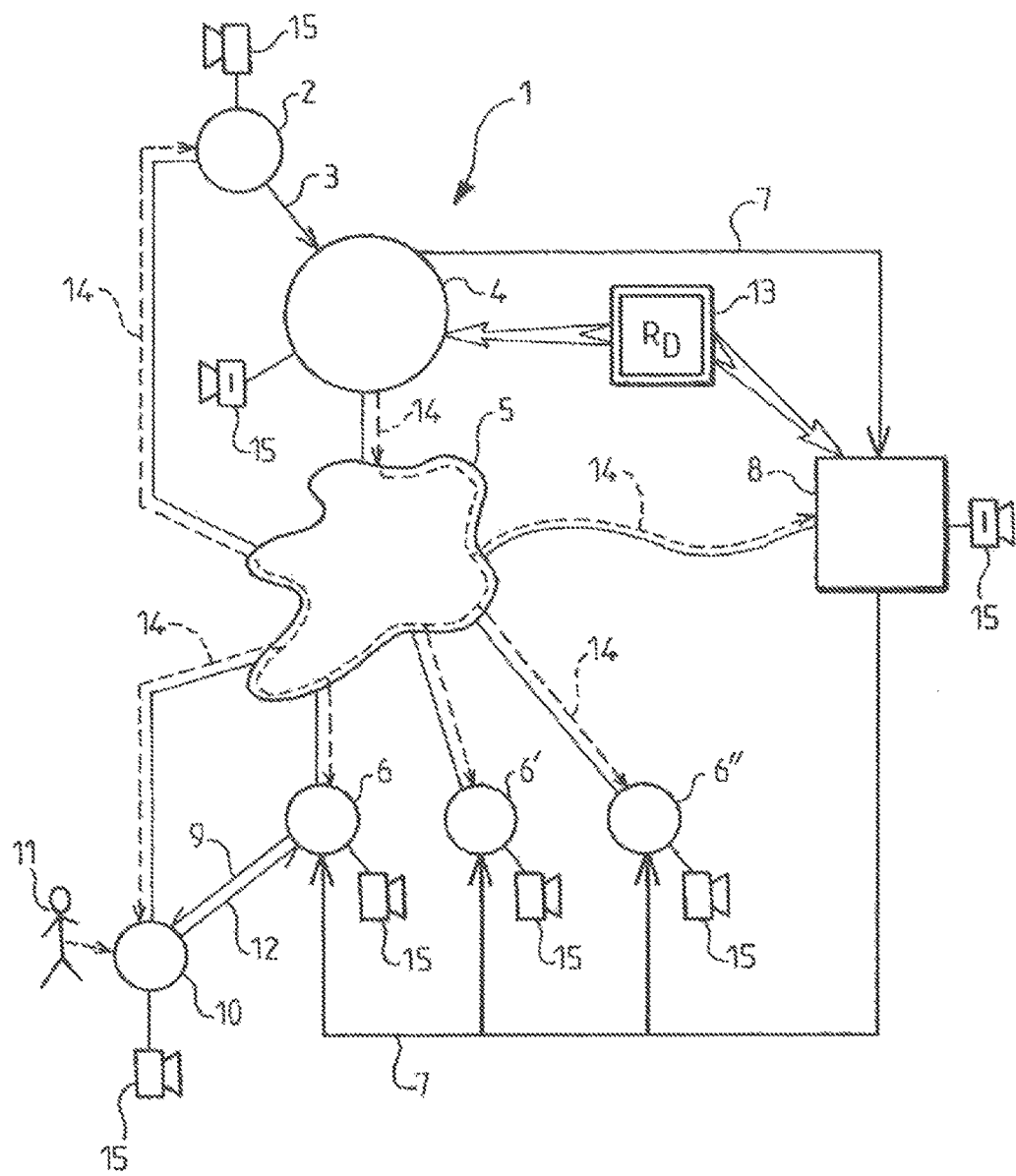
FIG. 1 is a general diagram illustrating principles of a method according to certain embodiments of the invention.

The products corresponding to a determined type, for example prostheses of the hip, left leg, made of titanium, of size Z, and produced at a manufacturer's facility 2, are delivered (arrow 3) to the supplier 4 of products, where they are packaged, marked with a first reference including a second reference $R_1$, $R_2$, etc., $R_i$ corresponding to the determined type, the references being stored in a first file called the supplier file.

Via the internet 5, by telephone, or by all other means, the products are then ordered by the user customer 6, 6', 6" (a hospital unit, a pharmacy dispensary, a doctor, etc.), then marketed (arrow 7) while storing the first references in a second file, associated with the user customers 6, 6', 6", etc. and with the supplier(s).

This storage in a second file can be carried out at the manufacturer's location 2, or at a third party (block 8).

On their arrival at the customers 6, 6', 6", the products are automatically detected and their references are stored in a third stock-management file.

During use, they are taken out (arrow 9), transmitted for use to 10 (for example the operating room) where they are automatically detected.

The chosen product is then taken by the patient or implanted into the sick person 11, the unused products being taken out again (arrow 12) while being redetected.

The information corresponding to the patients and to the implants is taken into account in order to form a fourth file, each associated with the use for a patient of the user customer concerned.

If one or more anomalies $R_D$ (block 13) are found making it possible to qualify a product of determined type as defective, data 14 (in dashed lines in FIG. 1) or a data stream (involving multiple packets) is automatically and simultaneously transmitted for example at the stage of the supplier 4 of the products, or at that of the storage 8 of the second file, for example via the internet. The transmitted data comprises the second reference associated with the type of defective product, to all the players 2, 6, 6', 6" etc., 10 (and if appropriate as a function of the location of initiation of the transmission, 4 or 8) for comparison. In the event of a positive comparison, an alarm 15 is then triggered at the players concerned.

In the rest of the description, the same reference numbers will be used to designate the same elements or elements that are identical or similar.

Figure 2:
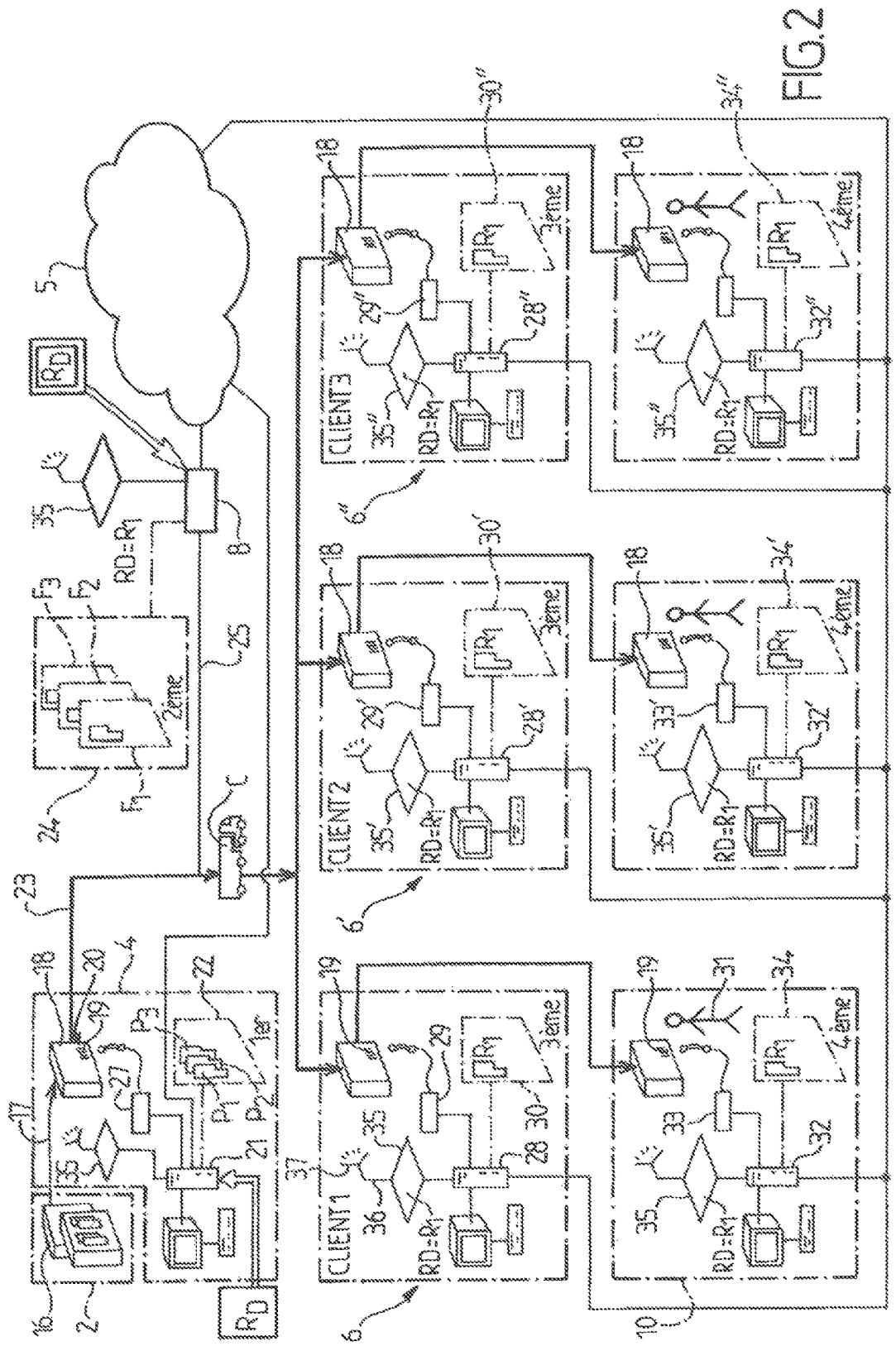
FIG. 2 shows schematically a system and its operation according to certain embodiments of the invention more particularly described here applied to medical products.

FIG. 2 illustrates certain embodiments of the invention more particularly described here.

Based on medical products 16 produced at a manufacturer's location 2 and ordered by the supplier 4 (arrow 17), the latter carries out the packaging 18 of the product and/or if the latter is already packaged, marks it with the first references 19 (e.g., colour code, barcode, addition of an RFID chip) in a manner known per se, in order to form the first references establishing a one-to-one relationship between an identifier and the medical product concerned.

The first references 19 include a second reference ($R_1$, $R_2$, $R_3$, etc.) corresponding to the determined type of product.

Given below is an example of a first reference including such a second reference for a knee prosthesis "right femoral implant."

It should be noted that the second reference may be included in and/or identical to the first reference.

These first references of the products (in this instance of the implants) and/or of their sealed packages are then entered in a computer 21 to form a first file 22 of references of the products, called the supplier file, of elements which are available and listed at the supplier 4, comprising the products $P_1$, $P_2$, $P_3$, etc., each including the appropriate second references $R_1$, etc. $R_i$.

For example $P_1$, $P_2$ and $P_3$ are three products having the same references $R_1$, or $P_1$ and $P_2$ have the second references $R_3$ and $P_3$ the second reference $R_2$ etc.

| "FILE NO. 1 OR SUPPLIER FILE" | | | |
|---|---|---|---|
| | Format | Width | Example |
| NAME OF THE PRODUCT $P_i$ | | | |
| Name | Alpha | 20 | Implant + right femoral |
| Product family | Alpha | 8 | TARTAR + |
| Type | Alpha | 10 | P0950D01 + |

| "FILE NO. 1 OR SUPPLIER FILE" -continued | | | |
|---|---|---|---|
| | Format | Width | Example |
| Kind | 999 | 3 | — * |
| Size | 99 | 2 | 45 * |
| Materials | Alpha | 10 | Titanium + |
| PRODUCT REFERENCE | | | |
| Manufacturer | 999 | 3 | — * |
| Supplier | 999 | 3 | — * |
| Production batch | Alphanum | 8 | 02P114 + |
| Size | Alphanum | 3 | H08 + |
| STERILIZATION | | | |
| Sterilization method | 99 | 2 | — |
| Validity of sterilization | yy mm | 4 | 06 12 |
| Sterilization batch | 99 | 2 | — * |

\* Supplier internal code
+ Included in the second references 20.

During the marketing of the products (bold arrow 23) the first references of the products $P_1$, $P_2$, etc. associated with the suppliers $F_1$, $F_2$, $F_3$, etc. and with the corresponding determined user customers 6, 6', 6", etc., for example of the surgical clinics, are then stored for example on a remote central server 8 (link 25), in a file 24 called FILE NO. °2 or CENTRAL FILE.

| "FILE NO. °2 OR CENTRAL FILE" | | | |
|---|---|---|---|
| | Format | Width | Example |
| NAME OF THE SUPPLIER | | | |
| SUPPLIER 1 Name of the customer | Alpha | 20 | IMPLANET |
| CUSTOMER 1 PRODUCT 1 | Alpha See FILE NO. °1 | 20 | Clinic X Y Z First reference abc with second reference $R_1$ |
| PRODUCT 2 | See FILE NO. °1 | | First reference cde with second reference $R_3$ |
| CUSTOMER NO. °2 | | | |
| PRODUCT 1 SUPPLIER 2 | See FILE NO. °1 | | |
| CUSTOMER NO. °5 PRODUCT 1 | Alpha See FILE NO. °1 | 20 | Hospital Z First reference abc with second reference $R_1$ |
| PRODUCT 2 | See FILE NO. °1 | | First reference xyz with second reference $R_2$ |
| SUPPLIER i | | | |
| CUSTOMER 1 PRODUCT 7 | Alpha | 20 | Doctor X First reference abc with second reference $R_5$ |

More precisely, at the time of the order via the internet network 5 and/or by other means, such as telephone, from a surgical clinic 6, 6', 6", the latter is entered onto the computer 21 which comprises means for computation, analyses, printing etc. of data corresponding to the order and to the types of implants ordered.

This order authorizes the taking out of the implants which are automatically taken into account by remote reading of the first references (barcode, RFID chip, etc.) via the device 27.

The data relating to the implants ordered and taken out for delivery are then, on the one hand and in the embodiment more particularly described here, transmitted to the remote central server 8 in order to form the CENTRAL FILE 24, for example depending on the administrative authority empowered to authorize or impose a recall, and on the other hand transmitted for confirmation via the internet to the computer 28, 28', 28", etc. of the clinic 6, 6', 6", etc.

The ordered products are then delivered (lorry C) to the clinic.

Hereafter, references x', x", etc. will not be listed. But it is quite evident that all the files and devices will be able to be multiplied in an identical manner in other locations and/or user customers.

On their arrival, the delivered products are automatically and remotely detected by the means 29 (e.g., bar code reader, RFID reader, smart card reader) situated at the customer in order to form a file 30 called "FILE NO. °3", for example of the type below.

| "FILE NO. °3" | | | |
|---|---|---|---|
| | Format | Width | Example |
| STORAGE ESTABLISHMENT | | | |
| Department | | | |
| Pharmacy | Alphanum | 8 | Block 2 |
| Surgery department | Alpha | 15 | Orthopaedics |
| Operating room | Alphanum | 8 | Room 3 |
| Date | | | |
| File created | dd mm yy | 6 | 15 01 06 |
| Movements | 99 | 2 | 03 |
| Last movement | dd mm yy | 6 | — ** |
| Name of the product | | | |
| Name | Alpha | 20 | Implant + right femoral |
| Product family | Alpha | 8 | TARTAR + |
| Type | Alphanum | 10 | P0950D01 + |
| Kind | 999 | 3 | — * |
| Size | 99 | 2 | 45 * |
| Materials | Alpha | 10 | Titanium + |
| Product reference | | | |
| Manufacturer | 999 | 3 | — * |
| Supplier | 999 | 3 | — * |
| Production batch | Alphanum | 3 | 02P114 + |
| Size | Alphanum | 3 | H08 + |
| Sterilization | | | |
| Sterilization method | 99 | 2 | — * |
| Validity of sterilization | aa mm | 4 | 06 12 |
| Sterilization batch | 99 | 2 | — * |

\* Supplier internal code
\*\* Hospital internal code
\+ Included in the second references When a surgeon 31 has to intervene in an operating room 10, the references 19 of the implants that are a priori necessary are detected by similar means programmed accordingly, namely means linked to a computer 32, for example a device 33 formed by a PDA or a barcode, RFID, and/or smartcard reader.

Usually there are several implants of different sizes, the choice of the effective size often being made at the last moment by the surgeon.

Simultaneously, and from a file called "PATIENT FILE" (not shown in the figure), internal to the hospital, comprising the sheets of the patients of the department (see for example below), the sheet of the patient to be operated on is taken from the computer 32 for example.

| "PATIENT FILE" | | | |
|---|---|---|---|
| | Format | Width | Example |
| NAME OF THE PATIENT | | | |
| Name | Alpha | 20 | Babar |
| Forename | Alpha | 20 | Milou |
| Date of birth | dd mm yy | 6 | 19 01 1954 |
| Place of birth | Alpha | 10 | Moulinsart |
| Social Security number | 9999999999 | 10 | xxxxxxxx |
| Address | Alphanum | 20 | 10 rue du Lavoir |
| Telephone number | 9999999999 | 10 | 01203240000 |
| E-mail | Alpha | 40 | xxxxx@xss.s |
| Surgical antecedent | Alpha | 40 | Appendicitis |
| Detrimental factors | Alpha | 30 | Haemophilia |
| SURGERY | | | |
| Establishment | Alphanum | 40 | NECKER |
| Department | Alphanum | 15 | Orthopaedics |
| Surgeon | Alpha | 20 | Ambroise Paré |
| Type of surgery | 999 | 3 | — ** |
| Location of surgery | Alpha | 20 | Right knee |

\*\* Hospital internal code

The surgeon operates and then returns the unused implants which in this embodiment are automatically detected remotely by the device 33, giving by difference the references of the implant that has been used.

The barcode or the identifier of the latter may also be read directly rather than obtained by difference.

A mixed sheet is then formed and used for updating the patient sheet above (the history of which will now contain the operation).

The following additional registers are then included to form, with the above PATIENT FILE, FILE NO. °4 according to certain embodiments of the invention more particularly described. (Sheet 34)

| Insertion of the implant | 999 | 3 | — ** |
|---|---|---|---|
| No comments | 999 | 3 | — ** |
| Difficulties | 9 | 1 | 5 ** |
| Name of the product | | | |
| Name | Alpha | 20 | Implant + right femoral |
| Product family | Alpha | 8 | TARTAR + |
| Type | Alphanum | 10 | P0950D01 + |
| Kind | 999 | 3 | — * |
| Size | 99 | 2 | 45 * |
| Materials | Alpha | 10 | Titanium + |
| Product reference | | | |
| Manufacturer | 999 | 3 | — * |
| Supplier | 999 | 3 | — * |
| Production batch | Alphanum | 3 | 02P114 + |
| Size | Alphanum | 3 | H08 + |

This FILE NO. °4 is then used to generate "FILE NO. °5" containing, for its part, partial references making it possible to maintain medical confidentiality of the patient involved in the operation and the first determined references of the implant used on him, including the second references.

| "FILE NO. °5" | | | |
|---|---|---|---|
| | Format | Width | Example |
| PATIENT | | | |
| One-to-one references corresponding to the patient | Alphanum | 20 | 570KB25700 |
| SURGERY | | | |
| Establishment | Alphanum | 40 | NECKER |
| Department | Alphanum | 15 | Orthopaedics |
| Surgeon | Alpha | 20 | — |
| Type of surgery | | | |
| Description | Alpha | 30 | — |
| DRG | | | — ** |
| Surgery location | Alpha | 20 | — |
| Limb | Alpha | 20 | Leg |
| Joint | Alpha | 20 | Knee |
| Right/left | Alpha | 1 | D |
| Implant insertion | 999 | 3 | — ** |
| No comment | 999 | 3 | — ** |
| Difficulties | 9 | 1 | 5 ** |
| Name of the product | | | |
| Name | Alpha | 20 | Implant + right femoral |
| Product family | Alpha | 8 | TARTAR + |
| Type | Alphanum | 10 | P0950D01 + |
| Kind | 999 | 3 | — * |
| Size | 99 | 2 | 45 * |
| Materials | Alpha | 10 | Titanium + |
| Product reference | | | |
| Manufacturer | 999 | 3 | — * |
| Supplier | 999 | 3 | — * |
| Production batch | Alphanum | 3 | 02P114 + |
| Size | Alphanum | 3 | H08 + |

** Hospital code
+ Included in the second references

This fifth file is then automatically or semi-automatically transmitted, for example for validation by a key on the part of the medical staff, via the network computer 28 to the supplier 4 via the internet network 5.

The information received is then processed at 21 by computer in order to allow the follow-up of the tracing of the implant according to the legal requirements and other operations such as a restocking order for example.

According to certain embodiments of the invention, if one or more anomalies are found making it possible to qualify a product 18 of determined type as defective, information $R_D$ received from the outside (double arrow) comprising the second reference $R_D$ of the defective product is automatically sent for example from the central server 8 to all of the media 21, 21', 21", etc. 28, 28', 28", etc. 32, 32', 32", etc.

On each of these media, the second reference $R_D$ of the defective product is compared (diamonds 35, 35', 35", etc.) in a manner known per se with the second references $R_1$, $R_2$, etc. appearing in the first, third, and fourth files.

The comparison may also be made in the second file, if the information $R_D$ comes from a supplier 4 for example.

In the event of a positive comparison (link 36), a warning signal is immediately triggered (siren 37) and an indication may be stored on the medium or media associated with the files involved in the positive comparison.

It is then possible to immediately block the product 18 corresponding to the second reference $R_1$ at all stages, including just before the operation for the surgeon 31.

It is also possible, with certain embodiments of the invention, to verify the case of incompatibility by comparison with a sixth file for example in the following form.

| "FILE NO. °6" | | | |
|---|---|---|---|
| | Format | Width | Example |
| PATIENT | | | |
| Name | Alpha | 20 | — |
| Forename | Alpha | 20 | — |
| Date of birth | dd mm yy | 6 | — |
| Place of birth | Alpha | 10 | — |
| Social Security number | 999999999 | 10 | — |
| Address | Alphanum | 20 | — |
| Telephone | 9999999999 | 10 | — |
| E-mail | Alpha | 40 | — |
| Type of allergy | | | |
| Description | Alpha | 30 | |
| Incompatibility | | | |
| Description | Alpha | 30 | |
| Type of incompatible product | | | |
| Product 1 | | | |
| Description | Alpha | 30 | |
| Second reference | Alpha | 30 | $R_1$ $R_2$ |

By comparing the second reference of the product to be implanted with the references of the products appearing in the incompatibility sheet of the patient (FILE NO. °6) it is then possible to prevent operating and/or treatment errors.

Figure 3:
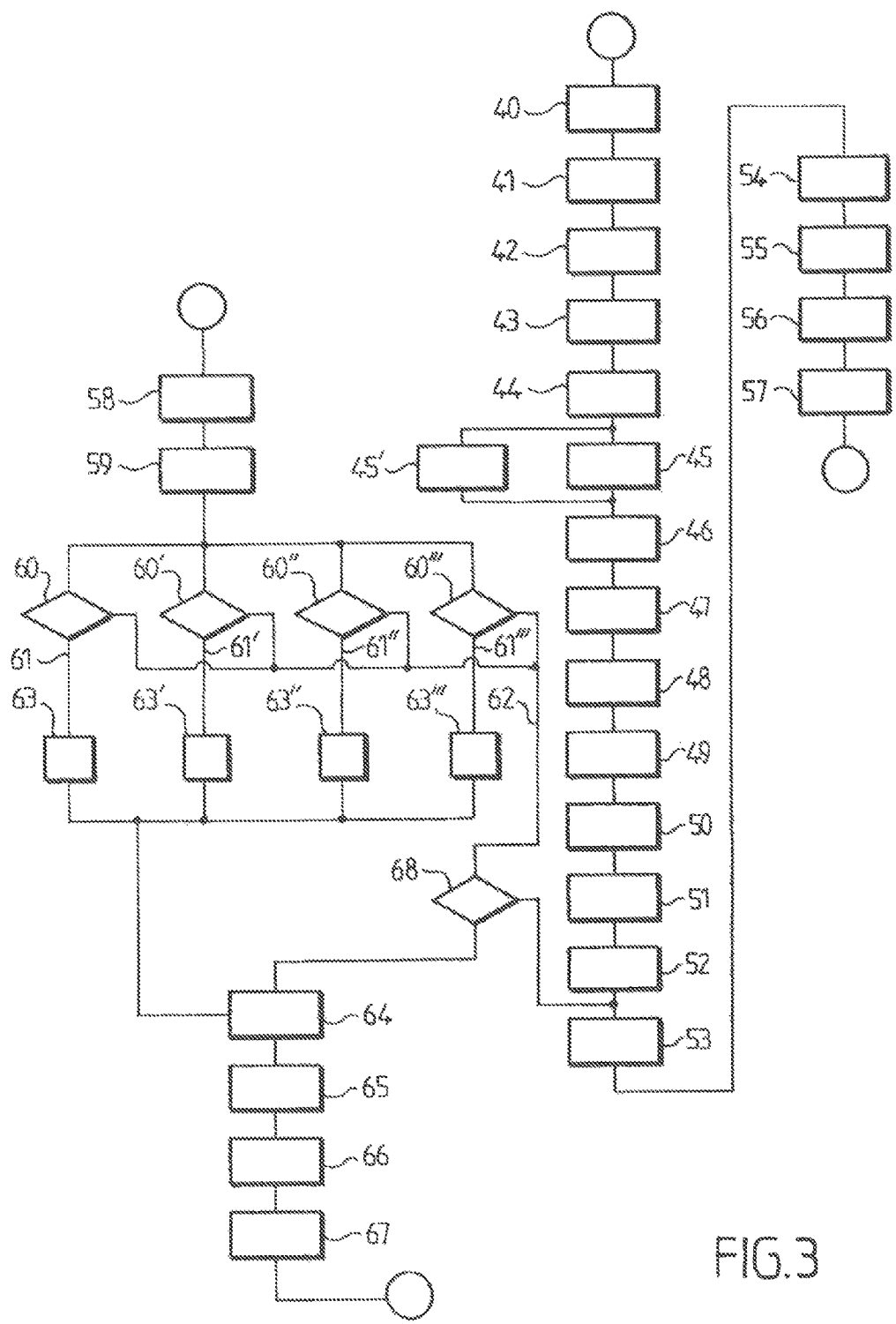
FIG. 3 is a block diagram showing the sequence of progression of the steps used in certain embodiments of methods of the invention more particularly described here.

The steps used in the invention in the embodiment more particularly described here will now be explained in detail with reference to the functional flowchart of FIG. 3.

After manufacture at 40 at the manufacturer's location of the implants concerned, a step of ordering by the supplier (step 41) is carried out. Then, the product having been delivered, it is stored at the supplier (step 42) who identifies it and marks it in a manner known per se (step 43).

Simultaneously, the supplier creates FILE NO. °1 or SUPPLIER FILE, as described above notably by identifying second references.

A step 44 of ordering by the hospital unit is then carried out, followed by the delivery (step 45).

In parallel with this delivery step, a step 45' is carried out for creating and/or completing FILE NO. °2 called MAIN FILE.

At the end of the delivery, FILE NO. °3 is created by remotely reading and entering (step 46) the implants inserted into the storage zone of the hospital unit, for example by reading a barcode and/or a remote smartcard reader.

During the use of an implant following a request from a surgeon, a step 47 of extracting the implants necessary for the operation is carried out with automatic detection at 48 of the implants by identical means.

At 49, FILE NO. °4, associated with the use of the implant for a patient, is completed based on the sheet of the patient (PATIENT FILE) belonging to the files of the hospital.

The operation by the surgeon is then carried out at 50, followed by the automatic detection at 51 of the implants that have not been used and that are therefore reentered into the storage system of the hospital unit.

Then a step 52 of creating FILE NO. °5 based on FILE NO. °4 is carried out, the file therefore being expurgated so as to preserve the medical confidentiality of the patient who has been operated on.

In other words, FILE NO. °5 therefore comprises information without names on the patient whose identity therefore remains confidential, and information on the implant that has been implanted in him.

A step 53 of transmission to the supplier of the elements of FILE NO. °5 will allow the comprehensive tracing of the implant including the operation on the patient.

There follows a step 54 of verification and storage of the files, and then of updating (step 55) of FILE NO. °1 of the implants at the supplier, optionally followed by a step 56 allowing the automatic order for the resupply of new implants following that which will be used during the operation, and a final optional step 57 of analysis generation and of statistics associated with the implants and/or with the types of operations associated with a certain type of sick person.

In parallel with this normal procedure of the ordering/procurement/use of an implant operation, the monitoring according to certain embodiments of the invention in the event of a defective product is implemented.

More precisely, if, at 58, one or more anomalies are found making it possible to qualify a product of determined type as defective, or in the case of a product that is manifestly incompatible with certain products already on the market, a data stream is automatically and simultaneously transmitted at 59 comprising the second reference for example and/or other information such as the first reference, the delivery date, the sterilization date and messages concerning what is to be done relative to these defective products.

Then simultaneously (or in a particular order sequentially), at 60, 60', 60", 60'", the second reference of the defective product is compared with the second references of the products appearing in the first, second, third and fourth files and a warning signal (link 61) is triggered in the event of a positive comparison, otherwise the continuation of the method (link 62) is pursued.

In the case of a positive comparison, a visual and/or audible signal is transmitted at 63, 63', 63", 63'" and (step 64) the product is blocked, the product being taken off the market at 65, by also transmitting (step 66) the necessary elements to the CENTRAL FILE at 67.

This blocking can be carried out also following a comparison at 68 with a FILE NO. °6 revealing the incompatibilities.

If there is no transmission following a negative comparison, the method returns to step 53 of transmission to the supplier of FILE NO. °5.

As goes without saying and as also results from the foregoing, the present invention is not limited to the embodiments more particularly described. On the contrary, it covers all the variants thereof and notably those in which the product is a medicine, a vaccine, or a series of medicines intended for complex and/or vital treatments such as for example against AIDS or the neuro-degenerative illnesses, such as Alzheimer's or Parkinson's.

It should be understood that the names used herein for the various types of files are for ease of reference only and do not in any way limit the scope of the claims.

Any or all of the functions and steps described herein may be embodied in computer-readable instructions and stored on a tangible medium, such as a memory, for execution by a processor. The functions may also be performed by one or more computers in combination, each having one or more associated memories storing instructions for performing the functions and networked as shown for example in FIG. 2.

The invention claimed is:

1. A method comprising:
storing, by a computer-based system and in a first file, a first reference with a software-enabled computer database link to a product, wherein the first file is a product reference file having product data for product referencing;
storing, by a computer-based system and in the first file, a second reference with a software-enabled computer database link to a product type;
storing, by a computer-based system and in a second file, the first reference with a software-enabled computer database link to a medical facility system and a supplier system, wherein the second file is a central file having centralized data;
storing, by a computer-based system and in a third file, the first reference with a software-enabled computer database link to the medical facility system, wherein the third file is a stock management file having stock data for managing stock;
storing, by a computer-based system and in a fourth file, the first reference with a software-enabled computer database link to a patient, wherein the fourth file is a patient file having patient data;
receiving, by the computer-based system, from a recall notification system and via an internet, data indicating that at least one of the first reference or the second reference has a defect;
implementing a software-enabled tag, by the computer-based system, on at least one of the first reference or the second reference with a defect indicator;
determining, by the computer-based system and via an internet, that the first file, the second file, the third file or the fourth file includes at least one of the first reference or the second reference;
updating, by the computer-based system and via the internet, the first file, the second file, the third file and the fourth file with a software-enabled computer defect alarm;
inserting, by the computer-based system and via the internet and based on the determining, into the first file and the second file a restriction indicator preventing the first file and the second file from creating at least one of the product or the product type;
inserting, by the computer-based system and via the internet, into the first file and the second file a recall indicator starting a recall procedure for at least one of the first reference or the second reference with the defect indicator;
inserting, by the computer-based system and via the internet and based on the determining, into the third file a removal indicator providing a notification to remove at least one of the first reference or the second reference with the defect indicator;
preventing, by the computer-based system and via the internet and using a software-enabled computer lock, input of at least one of the first reference or the second reference with the defect indicator into the fourth file; and
blocking, by the computer-based system, a use of the product in response to reading a radio frequency identification tag (RFID) tag on the product, wherein the RFID tag is associated with the defect indicator.

2. The method of claim 1, further comprising:
creating, by the computer-based system, a fifth file containing the first references and a subset of data from the fourth file, wherein the subset of data maintains patient confidentiality;
transmitting, by the computer-based system and based on the determining, the fifth file to the second file for monitoring of the fifth file;

creating, by the computer-based system, a sixth file containing the first references that are incompatible with products corresponding to the second references;

comparing, by the computer-based system and during the monitoring, the first references of the fifth file to the first references of the sixth file to determine that the first references are incompatible;

implementing the software-enabled tag, by the computer-based system, on the first reference with an incompatible indicator; and preventing, by the computer-based system, the fourth file from accepting input of the first reference with the incompatible indicator.

3. The method of claim 2, further comprising:

storing, by the computer-based system and in a seventh file, the first reference and characteristics of the product;

comparing, by the computer-based system, the seventh file with the fourth file;

identifying, by the computer-based system and based on the comparison, incompatibility risks for the patient;

implementing the software-enabled tag, by the computer-based system, on the first reference with an incompatibility risk indicator; and preventing, by the computer-based system, the fourth file from accepting input of the first reference with the incompatibility risk indicator.

4. The method of claim 3, wherein the seventh file is located in a packaging for the product.

5. The method of claim 4, further comprising determining the products with a software-enabled computer database link to the defect indicator that at least one of are in transit to a medical facility, are in stock at the medical facility or have been used by patients.

6. A method comprising:

receiving, by the computer-based system and via the internet, defect data indicating that at least one of a first reference with a software-enabled computer database link to a product has a defect or a second reference with a software-enabled computer database link to a product type has the defect;

implementing a software-enabled tag, by the computer-based system, on at least one of the first reference or the second reference with a defect indicator;

wherein the first reference and the second reference are stored in a first file, wherein the first file is a product reference file having data for product referencing;

wherein the first reference with a software-enabled computer database link to a medical facility system and a supplier system is stored in a second file, wherein the second file is a central file having centralized data;

wherein the first reference with a software-enabled computer database link to the medical facility system is stored in a third file, wherein the third file is a stock management file having stock data for managing stock;

wherein the first reference with a software-enabled computer database link to a patient is stored in a fourth file, wherein the fourth file is a patient file having patient data;

determining, by the computer-based system, that the first file, the second file, the third file or the fourth file includes at least one of the first reference or the second reference;

updating, by the computer-based system and via an internet, the first file, the second file, the third file and the fourth file with a software-enabled computer defect alarm;

inserting, by the computer-based system and via the internet, into the first file and the second file a restriction indicator preventing the first file and the second file from creating at least one of the product or the product type;

inserting, by the computer-based system and via the internet, into the first file and the second file a recall indicator starting a recall procedure for at least one of the first reference or the second reference with the defect indicator;

inserting, by the computer-based system and via the internet and based on the determining, into the third file a removal indicator providing a notification to remove at least one of the first reference or the second reference with the defect indicator;

preventing, by the computer-based system and via the internet and using a software-enabled computer lock, input of at least one of the first reference or the second reference with the defect indicator into the fourth file; and blocking, by the computer-based system, a use of the product in response to reading a radio frequency identification tag (RFID) tag on the product, wherein the RFID tag is associated with the defect indicator.

7. The method of claim 6, wherein the software-enabled computer defect alarm includes at least one of a visual indicator or an audible indicator.

8. The method of claim 6, further comprising preventing modification of the fourth file.

9. The method of claim 6, further comprising storing an indicator that the product is defective on one or more computer-readable media with a software-enabled computer database link to one or more of the first file, the second file, the third file, and the fourth file.

10. The method of claim 6, wherein the first file includes a list of products available from a supplier associated with the supplier system.

11. The method of claim 6, wherein the second file includes a list of users of products and a corresponding list of products ordered by each user.

12. The method of claim 6, wherein the third file includes a list of products received by a user from a supplier associated with the supplier system.

13. The method of claim 6, wherein the fourth file includes patient information for a patient and product information for a product associated with the patient.

14. The method of claim 6, further comprising:

creating, by the computer-based system, a fifth file containing the first references and a subset of data from the fourth file, wherein the subset of data maintains patient confidentiality;

transmitting, by the computer-based system and based on the determining, the fifth file to the second file for monitoring of the fifth file;

creating, by the computer-based system, a sixth file containing the first references that are incompatible with products corresponding to the second references;

comparing, by the computer-based system and during the monitoring, the first references of the fifth file to the first references of the sixth file to determine that the first references are incompatible;

implementing the software-enabled tag, by the computer-based system, on the first reference with an incompatible indicator; and preventing, by the computer-based system, the fourth file from accepting input of the first reference with the incompatible indicator.

15. The method of claim 6, further comprising:

storing, by the computer-based system and in a seventh file, the first reference and characteristics of the product;

comparing, by the computer-based system, the seventh file with the fourth file;

identifying, by the computer-based system and based on the comparison, incompatibility risks for the patient;

implementing the software-enabled tag, by the computer-based system, on the first reference with an incompatibility risk indicator; and preventing, by the computer-based system, the fourth file from accepting input of the first reference with the incompatibility risk indicator.

16. The method of claim 15, further comprising preventing modification of the fourth file.

17. The method of claim 15, further comprising storing an indicator that the product is defective on one or more computer-readable media with a software-enabled computer database link to one or more of the first file, the second file, the third file, and the fourth file.

18. The method of claim 6, further comprising analyzing, by the computer-based system, one or more of the first file, the second file, the third file, and the fourth file to identify a defective product that has already been used.

19. The method of claim 6, further comprising analyzing, by the computer-based system, one or more of the first file, the second file, the third file, and the fourth file to identify a defective product that is in stock with a user or a supplier associated with the supplier system.

20. The method of claim 6, further comprising analyzing, by the computer-based system, one or more of the first file, the second file, the third file, and the fourth file to identify a defective product that is in transit to a user or a supplier associated with the supplier system.

* * * * *